United States Patent [19]

Gingras

[11] Patent Number: 4,996,978
[45] Date of Patent: Mar. 5, 1991

[54] BACK SUPPORT ASSEMBLY

[76] Inventor: Eric A. Gingras, 1185 Shelburne Rd., #102, South Burlington, Vt. 05403

[21] Appl. No.: 340,669

[22] Filed: Apr. 20, 1989

[51] Int. Cl.$^5$ ............................................. A61F 5/01
[52] U.S. Cl. ...................................... 128/78; 135/68; 297/411
[58] Field of Search .......................... 128/78; 297/411; 135/68, 73

[56] References Cited

U.S. PATENT DOCUMENTS

| 32,014 | 4/1861 | Taylor | 128/78 |
| 3,213,870 | 10/1965 | Kiehn | 128/78 |
| 3,304,946 | 2/1967 | Lutes | 135/73 X |
| 4,565,409 | 1/1986 | Hollonbeck et al. | 297/411 |

FOREIGN PATENT DOCUMENTS

| 1375351 | 9/1964 | France | 128/78 |
| 1266 | 3/1883 | United Kingdom | 128/78 |

Primary Examiner—Edgar S. Burr
Assistant Examiner—Moshe I. Cohen
Attorney, Agent, or Firm—Thomas N. Neiman

[57] ABSTRACT

The assembly comprises at least one back support crutch that provide support while the user is in the seated position. Each of the crutches has a body support brace and an arm support support brace. Each crutch has a width adjustment mechanism and a height adjustment mechanism. These adjustments permit the user to take the weight off the spine and buttocks and, at the same time, allow the assembly to be used by all sizes of individuals. The body support brace and arm support brace have swivel hinges that allow the user to comfortably position the assembly for optimum comfort. Handle grips are provided and are adjustable to permit the user to place his or her hands in the most comfortable position, while maintaining their elbows in a relatively constant support location.

7 Claims, 1 Drawing Sheet

BACK SUPPORT ASSEMBLY

This invention pertains to medical support devices, and in particular to such orthopedic medical support devices that can be used to relieve back pain by taking stress off the back and spine of an individual while in the sitting position.

The field of support is old and has many applications. The most common example is the use of a crutch by an individual with a broken leg to keep the weight of the individual's body off the injured limb, in order to assist and speed up the healing process for the limb. A number of devices have been developed to aid individuals with back problems, i.e. back operations, spinal difficulties, etc. Examples of these devices include the Canadian Patent issued to Ernest Dustin, π510,854 issued on 15 Mar. 1955 for a Body Support and Weight Distributor. This device provides a solid support for the upper body by placing the weight of the upper body on supports under the armpit area and adds additional support by providing a collar around the neck. Another example of a device which provides support for the upper body is the U.S. Pat. No. 4,565,409 issued to Gary G. Hollonbeck et. al., for a Body Support Apparatus, issued on 21 Jan. 1986. This device teaches a pair of adjustable crutches that are designed to be used while seating. The crutches provide support for the upper body at the armpit area. The limitations of these devices are that they concentrate the individual's upper body weight in a single centralized location, rather then spread the weight around to provide for a more comfortable, evenly distributed support.

Clearly, it is desirable for a orthopedic medical support device that does not contain the limitations described above and at the same time is simple and practical to operate. It is the object of this invention, then to set forth an improved medical support device which avoids the disadvantages limitations, above-recited, which obtain in medical support device.

It is also the object of this invention to teach a back support assembly which is simple to install and use and that will enable individuals of all sizes to use the assembly. It is another object of this invention to teach a back support assembly that distributes the individual's upper body weight over a broad area of the arms and sides of the user while he or she is in the seated position. Particularly, it is the object of this invention to set forth a back support assembly, for relieving pressure from an individual's back and spine while in the seated position, comprising at least one frame; said frame comprising vertical support means; said frame having a base support means; said frame further having height adjustment means for providing the proper support height for the assembly; said height adjustment means having locking means; body support means; said body support means having pivot means; arm support means; said arm support means having grasping means for allowing the wrist and hand to be sustained in a comfortable position; said grasping means having pivot means; said frame having width adjustment means; and said width adjustment means having locking means.

Further objects and features of this invention will become more apparent by reference to the following description taken in conjunction with the accompanying figures, in which.

Figure 4:
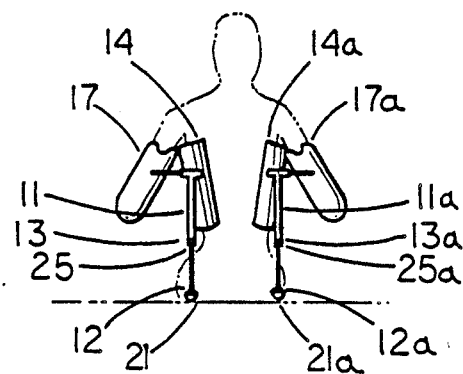
FIG. 4 is a perspective view of the novel assembly in proper position for use.
Figure 3:
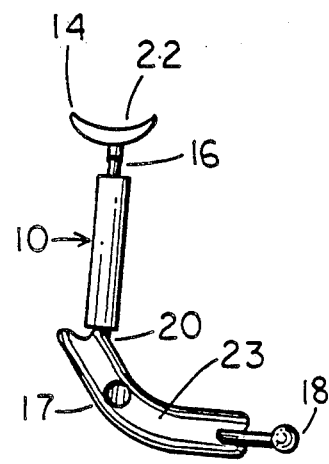
FIG. 3 is a top view thereof.
Figure 1:
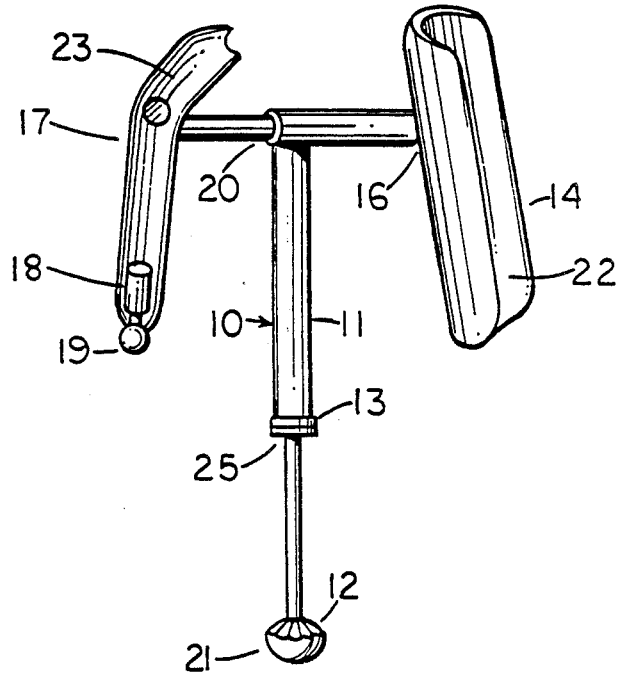
FIG. 1 is a frontal view of one side of the novel back support assembly.
Figure 2:
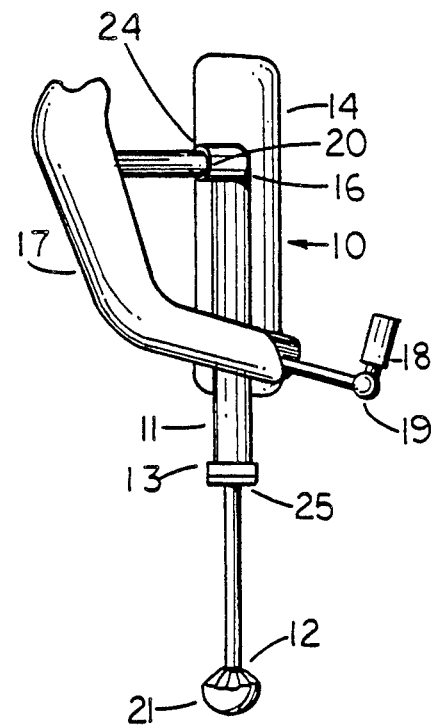
FIG. 2 is a side elevational view thereof.

As shown in the figures, the back support assembly 10 comprises a frame 11 and 11a. The frame 11 and 11a has a rounded base 12 and 12a which is covered with a non-skid surface 21 and 21a. The frame 11 and 11a has a height adjustment device 13 and 13a. This device comprises a tension regulating height adjustment lock 25 and 25a are provided to maintain the proper height position. By adjusting the height of the device the user can relieve the weight of the trunk of the upper body off the back and the spine. Each of the frames have a body support brace 14 and 14a which are formed molds that are covered with a soft pad 22 and 22a for comfort. The body support braces 14 and 14a have body support pivots 16 and 16a positioned at the point where the brace contacts the frame. This pivot allows the user to have the body support brace in the most comfortable position for long term use.

The frames 11 and 11a also have arm support braces 17 and 17a which are formed molds that have pads 23 and 23a. These braces are heavily padded in the elbow area in order to provide a great deal of comfort for the user. Each of the arm braces 17 and 17a have support handles 18 and 18a which are mounted on handle pivots 19 and 19a. The handles provide a great deal of support for the user and the handle pivots allow the user to change his or her hand position, while at the same time maintaining his or her elbows in the most comfortable position. The frames 11 and 11a also have a width adjustment device 20 and 20a that allows users of all sizes to use the assembly. The width adjustment device comprises a tension regulating locking assembly. A width adjustment lock 24 and 24a is provided in order to maintain the proper width adjustment. This lock comprises a pressure tensioning collar.

In operation, the user with a back problem can use the back support assembly to sit comfortably by relieving the pressure of the weight of the upper body from the spine and buttocks and distribute this pressure on the sides, arms, elbows and hands and away from being concentrated in the armpit area. The user adjusts the width adjustment to the proper distance and then locks that adjustment in that position. The height adjustment device is set so that pressure is relieved from his or her spine and buttocks and that position is locked. The user then sits with his or her arms in the arm braces and the body braces positioned along the side of the body. The individual's hands grasp the support handles. This arrangement provides a great deal of comfort and relief for those individuals with back problems.

While I have described my invention in connection with specific embodiments thereof, it is clearly to be understood that this is done only by way of example and not as a limitation to the scope of my invention as set forth in the objects thereof and in the appended claims.

I claim:

1. A back support assembly, for relieving pressure from an individual's back and spine while in the seated position, comprising:
   at least one frame;
   said frame comprising vertical support means;
   said frame having a base support means;
   said frame further having height adjustment means for providing the proper support height for the assembly;

said height adjustment means having locking means;
body support means;
said body support means having pivot means;
arm support means;
said arm support means comprises a formed padded mold for providing a prime means of support for the user of said assembly;
said arm support means having grasping means attached for allowing the wrist and hand to be sustained in a comfortable position;
said grasping means having pivot means for providing said user to have the flexibility to place said grasping means in the optimum position for support and comfort;
said frame having width adjustment means; and
said width adjustment means having locking means.

2. A back support assembly, according to claim 1, wherein:
said base support means comprising a broadened, rounded block; and
said block having a non-skid surface thereon.

3. A back support assembly, according to claim 1, wherein:
said height adjustment means comprising a threaded rod for screwing said vertical means to the optimum position.

4. A back support assembly, according to claim 1, wherein:
said height adjustment locking means comprising an increasing pressure collar.

5. A back support assembly, according to claim 1, wherein:
said body support means comprising a formed padded mold.

6. A back support assembly, according to claim 1, wherein:
said grasping means means comprising a handle.

7. A back support assembly, according to claim 1, wherein:
said width adjustment locking means comprising an increasing pressure collar.

* * * * *